(12) United States Patent
Groves et al.

(10) Patent No.: US 7,684,540 B2
(45) Date of Patent: Mar. 23, 2010

(54) APPARATUS AND METHOD FOR FLUID PHASE FRACTION DETERMINATION USING X-RAYS

(75) Inventors: Joel Groves, Leonia, NJ (US); Etienne Vallee, Princeton, NJ (US); Peter Wraight, Skillman, NJ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 60 days.

(21) Appl. No.: 11/425,285

(22) Filed: Jun. 20, 2006

(65) Prior Publication Data

US 2007/0291898 A1   Dec. 20, 2007

(51) Int. Cl.
*G01N 23/06* (2006.01)
(52) U.S. Cl. .............................. 378/53; 378/44; 378/45; 378/47; 378/51
(58) Field of Classification Search .................... 378/44, 378/45, 47, 51, 53, 109–112
See application file for complete search history.

(56) References Cited

U.S. PATENT DOCUMENTS

| | | | |
|---|---|---|---|
| 4,490,609 A | | 12/1984 | Chevalier |
| 5,164,590 A | | 11/1992 | Coles et al. |
| 5,247,559 A | | 9/1993 | Ohtsuchi et al. |
| 5,479,020 A | | 12/1995 | Mohn |
| 5,591,922 A | | 1/1997 | Segeral et al. |
| 5,680,431 A | | 10/1997 | Pietras, III et al. |
| 5,689,540 A | * | 11/1997 | Stephenson et al. ........... 378/53 |
| 5,742,660 A | | 4/1998 | Majewski et al. |
| 5,778,041 A | | 7/1998 | Chase et al. |
| 5,854,820 A | | 12/1998 | Slijkerman et al. |
| 6,097,786 A | * | 8/2000 | Groves et al. ................. 378/53 |
| 6,182,505 B1 | | 2/2001 | Segeral |

(Continued)

FOREIGN PATENT DOCUMENTS

EP    0612407 B1    9/1997

(Continued)

OTHER PUBLICATIONS

Abouelwafa et al., The measurement of component ratios in multiphase systems using gamma ray attenuation, 1980, J. Phys. E: Sci. Instrum., vol. 13, pp. 341-345.*

(Continued)

*Primary Examiner*—Hoon Song
*Assistant Examiner*—Mona M Sanei
(74) *Attorney, Agent, or Firm*—Myron Stout; Kevin B. McGoff (57) ABSTRACT

An apparatus and method for determining the phase fraction of a fluid collected downhole is shown comprising an x-ray generator, a filter, a sample cell, and a radiation detector. The filter produces a radiation spectrum with a high energy portion and a low energy portion. Filtered radiation is passed through a sample fluid and the resulting attenuated radiation signal is used in calculating the phase fractions of oil, water, and gas in the sample fluid. In one embodiment, a second reference radiation detector measures the radiation directly from the x-ray generator and this measurement is used in normalizing the fraction result. The ratio of the high energy signal to low energy signal of the reference detector is used in controlling the input voltage of the x-ray generator thus ensuring a stable spectrum.

13 Claims, 6 Drawing Sheets

U.S. PATENT DOCUMENTS

| | | |
|---|---|---|
| 6,265,713 B1 | 7/2001 | Berard et al. |
| 6,286,367 B1 | 9/2001 | Segeral |
| 6,378,380 B1 | 4/2002 | Kusters et al. |
| 6,389,908 B1 | 5/2002 | Chevalier et al. |
| 6,405,604 B1 | 6/2002 | Berard et al. |
| 6,755,086 B2 | 6/2004 | Salamitou et al. |
| 2003/0106993 A1 | 6/2003 | Chen et al. |
| 2005/0031074 A1 | 2/2005 | Fitzgerald |
| 2005/0163284 A1* | 7/2005 | Inazuru ............ 378/108 |
| 2006/0067473 A1* | 3/2006 | Eberhard et al. ....... 378/98.9 |
| 2006/0072703 A1* | 4/2006 | Naidu et al. ........... 378/101 |

FOREIGN PATENT DOCUMENTS

| | | |
|---|---|---|
| EP | 0896666 B1 | 7/2002 |
| EP | 0684458 B1 | 12/2002 |
| GB | 2289766 A | 11/1995 |
| WO | 9310439 A1 | 5/1993 |
| WO | WO 94/25859 * | 10/1994 |
| WO | 0196902 A2 | 12/2001 |
| WO | 03019118 A1 | 3/2003 |

OTHER PUBLICATIONS

U.S. Appl. No. 09/753,859, filed Jan. 3, 2001, Perciot, et al.

Atkinson, et at, "A New Horizon in Multiphase Flow Measurement," Oilfield Review (Winter 2004/2005), vol. 16, No. 4, Schlumberger, pp. 52-63.

* cited by examiner

APPARATUS AND METHOD FOR FLUID PHASE FRACTION DETERMINATION USING X-RAYS

BACKGROUND

This disclosure relates to an apparatus and method for fluid phase fraction determination using x-rays. More specifically, this disclosure relates to system for determining phase fractions in fluid using a dual peak radiation spectrum directed through a sample of interest and radiation detectors measuring the resultant radiation signal.

Knowing the phase fraction of a fluid can provide important information in the oil industry. Fraction determination is useful in determining a multiphase flow rate. Multiphase flow metering can provide the industry with high performance oil and gas testing service, both in permanent monitoring, such as Schlumberger's PhaseWatcher tool, and periodic testing, such as Schlumberger's PhaseTester.

Typically, formation fluid comprises oil, gas, and water in some combination. Certain well operations involve pumping fluid into an adjacent well or borehole to help force subterranean fluid from the primary borehole. A phase fraction meter will be useful in real-time to show when the primary borehole is perforated and unwanted fluids are leaking into the fluid of interest. This information is also useful in optimizing the production of the reservoir. The water to liquid ratio is very important and constant monitoring can allow for the best utilization of the well resources.

Additionally, fluid that is high in water content will be of less monetary worth than fluid high in one of the other components. By determining this fraction early in the collection process, it is possible to quickly estimate the value of any given operation. By testing fluid when delivered by an unknown source, it can be determined if the fluid fraction promised is what is being provided.

One approach in the prior art utilized a separator or a large tank used to physically store some amount of fluid from a well and segregate the phases through a gravity based process. This requires stable conditions inside the separator that may take hours to obtain. This stability may be difficult or even impossible to obtain and creates a bottleneck because flow must be stopped during the testing process. Separator-based systems also lead to error when there is some commingling of the phases. Additionally, viscous fluids such as heavy oil make accurate separation and testing difficult.

Later, certain envisioned systems attempted to alleviate these problems and allow for real-time phase fraction determination using a radiation source and detector. These fraction meters used chemical radiation sources and were often deployed for long periods of time in unattended locations. The locations often are not secure and may encounter fluctuating environmental conditions. This instability created a desire to use non-chemical sources for the input of radiation. However, there are certain benefits to the use of chemical sources. Specifically, the degradation of their output radiation over time is stable allowing them to provide a highly predictable radiation signal. An electrical radiation generator would alleviate some of these concerns, but most electrical photon generators (such as x-ray generators) are subject to issues such as voltage and beam current fluctuation.

Other prior art envisioned the use of an x-ray generator to create radiation. An example of this approach is shown in U.S. Pat. No. 5,689,540 to Stephenson et al. and assigned to Schlumberger Technology Corporation of common assignment with the subject application. The disclosure of this patent is hereby incorporated by reference as though set forth at length. This invention describes a system for sending a single radiation spectrum through a fluid sample and detecting the attenuated radiation to determine a fluid fraction.

Although the Stephenson et al. system has many advantages as directly and inherently disclosed in that patent, room for improvement remains. First, it is desired to provide a multiphase fluid fraction meter than can be used in a wide range of locations including installed at remote locations, in laboratories, and in portable placements. Second, it is desired to send a radiation spectrum through that comprises a high energy level portion and a low energy level portion to allow for the three fluid phase fractions of interest to be determined. Third, it is desirable to provide a system capable of maintaining a stable voltage and beam current over time. A varying voltage can change the output spectrum of the x-ray generator and make the resultant radiation signal less useful.

BRIEF SUMMARY OF THE INVENTION

In consequence of the background discussed above, and other factors that are known in the field of fluid fraction determination, applicants recognized a need for an apparatus and method for determining the phase fraction of a fluid sample. Applicants recognized that an x-ray generator with a carefully controlled acceleration voltage and beam current could be used along with one or more radiation detectors to provide a reliable measure of the sample phase fraction for oil, water, and gas.

One embodiment comprises a method and apparatus for determining the oil, water, and gas fractions of a fluid. In one aspect, an x-ray generator provides radiation input that is filtered to produce a spectrum with distinct high energy and low energy regions. The filtered radiation is introduced to two channels, one passing through a fluid housed in a measurement cell and passed to a first radiation detector and the other passed directly to a second radiation detector. The measurements of the two radiation detectors are used in analysis to determine the phase fractions of the sample fluid and possibly provide insight regarding changes in composition. Additionally, the output of the second radiation detector is used in controlling the acceleration voltage and beam current of the x-ray generator to ensure an accurate signal over time.

THE DRAWINGS

The accompanying drawings illustrate embodiments of the present invention and are a part of the specification. Together with the following description, the drawings demonstrate and explain principles of the present invention.

DETAILED DESCRIPTION

Figure 1:
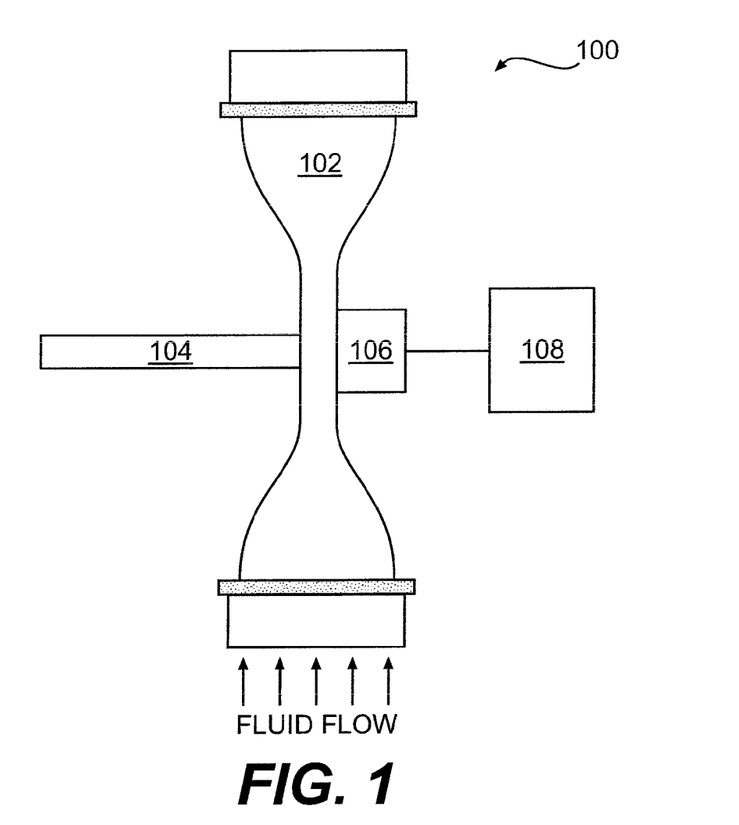
FIG. 1 is a schematic view of the operational context in which the present apparatus and method can be used to advantage.

Referring now to the drawings and particularly to FIG. 1 wherein like numerals indicate like parts, there is shown a schematic illustration of an operational context of the instant invention. In one embodiment the apparatus 100 for determining a fluid phase fraction of a sample fluid is shown. Sample formation fluid (schematically illustrated by directional arrows in FIG. 1) collected from the formation flows through sample cell 102. In this embodiment, the sample cell is a venturi chamber, the use of a venturi chamber is not required in all applications, a regular pipe may be used. The sample fluid may be stored in a laboratory, collected directly from a well in production, collected in testing a newly drilled well, or any other scenario in which fluid is collected or stored. While sample fluid flows through the sample cell 102, x-ray generator 104 produces radiation in response to an input voltage. This radiation is passed from the x-ray generator 104, through the sample cell and measured by radiation detection section 106. In one embodiment, radiation is also sent directly from x-ray generator 104 to detector section 106 for use as a reference. The use of an x-ray generator 104 and radiation detector section 106 allows for the reliable determination of the phase fraction of the sample fluid in sample cell 102. The output of radiation detector section 106 is transmitted to control and acquisition system 108. This system may also use outputs of radiation detector section 106 to control the acceleration voltage and beam current of x-ray generator 104. Due to the fast flow of fluid through many of these systems (approximately 20 m/s in some situations) measurements are often made in short increments to provide a profile of phase fractions over time. However, any single measurement can show the phase fractions of water, oil, and gas in the sample cell at that point in time.

Some examples of scenarios in which this invention is advantageous include permanent monitoring, mobile testing, laboratory testing, and artificial lift optimization. Those of ordinary skill in the art will recognize that these are merely examples of possible uses and the above examples are not exhaustive.

X-Ray Physics

X-ray tubes produce x-rays by accelerating electrons into a target via a high positive voltage difference between the target and electron source. The target is sufficiently thick to stop all the incident electrons. In the energy range of interest, the two mechanisms that contribute to the production of x-ray photons in the process of stopping the electrons are X-ray fluorescence and Bremsstrahlung radiation.

X-ray fluorescence radiation is the characteristic x-ray spectrum produced following the ejection of an electron from an atom. Incident electrons with kinetic energies greater than the binding energy of electrons in a target atom can transfer some (Compton Effect) or all (Photoelectric Effect) of the incident kinetic energy to one or more of the bound electrons in the target atoms thereby ejecting the electron from the atom.

If an electron is ejected from the innermost atomic shell (K-Shell), then characteristic K, L, M and other x-rays are produced. K x-rays are given off when an electron is inserted from a higher level shell into the K-Shell and are the most energetic fluorescence radiation given off by an atom. If an electron is ejected from an outer shell (L, M, etc.) then that type of x-ray is generated. In most cases, the L and M x-rays are so low in energy that they cannot penetrate the window of the x-ray tube. In order to eject these K-Shell electrons, an input of more than 80 kV is required in the case of a gold (Au) target due to their binding energy.

Another type of radiation is Bremsstrahlung radiation. This is produced during the deceleration of an electron in a strong electric field. An energetic electron entering a solid target encounters strong electric fields due to the other electrons present in the target. The incident electron is decelerated until it has lost all of its kinetic energy. A continuous photon energy spectrum is produced when summed over many decelerated electrons. The maximum photon energy is equal to the total kinetic energy of the energetic electron. The minimum photon energy in the observed Bremsstrahlung spectrum is that of photons just able to penetrate the window material of the x-ray tube.

The efficiency of converting the kinetic energy of the accelerated electrons into the production of photons is a function of the accelerating voltage. The mean energy per x-ray photon increases as the electron accelerating voltage increases.

A Bremsstrahlung spectrum can be altered using a filter and by changing (1) the composition of the filter, (2) the thickness of the filter, and (3) the operating voltage of the x-ray tube. The embodiment described herein utilizes a single filter to create low and high energy peaks from the same Bremsstrahlung spectrum. Specifically, a filter is used to provide a single spectrum with a low energy peak and a high energy peak.

Figure 2:
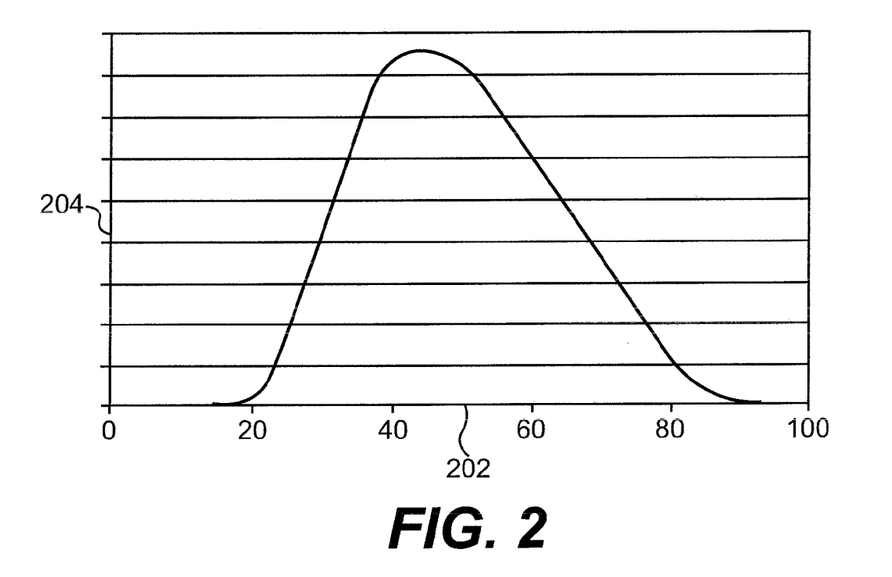
FIG. 2 is a graphic representation of a radiation energy spectrum output by an x-ray generator.

FIG. 2 shows the Bremsstrahlung radiation spectrum. Ordinate axis 202 represents energy measured in keV. Abscissa axis 204 is the count rate or the number of photons per second per keV that are incident on a radiation detector. This input radiation is filtered as described above.

X-ray Fluid Phase Fraction Meter

Generating radiation using an x-ray generator to perform fluid phase fraction determination is desirable for a number of reasons. The radiation flux available and the need for photons with a quite low energy (<100 keV) make this type of radiation source well suited for the application. Measurement of the attenuation level is performed at two different mean energy levels: a high energy level where the photon attenuation occurs predominately from Compton Scattering with some photoelectric absorption and a low energy level where photon attenuation occurs from Compton Scattering and the Photoelectric Effect and the absorption by the Photoelectric Effect is stronger than in the case of the high energy. In addition to the two energy levels, in order to have a robust measurement system, it is necessary to have a detection of radiation passing through a substance that will cause attenuation as well as a detection of radiation passing through air. The first of these is found by a measurement radiation detector and the second is found by a reference radiation detector.

The attenuation of a beam of x-rays of energy E, intensity $I_0(E)$, passing through a thickness 'd' of material with a density 'ρ' can be written $$I(E) = I_0(E) e^{-\mu_m(E)\rho d}$$

where any interaction of the photons traversing the material attenuates the beam. Here, $\mu_m(E)$ is the mass attenuation coefficient of the material. It is important to note that this mass attenuation coefficient is variable depending on the type of oil, gas and water that is present. To find the three values, calibration testing is often performed or, alternatively, a series of calculations is made based on the known chemistry of the fluid that is present. I(E) in the previous equation does not include the detection of photons created following photoelectric absorption or multiple scattered photons.

In order to determine the phase fractions of oil, gas, and water in a sample fluid, it is necessary to take attenuation measurements at a high energy and a low energy. In the instant invention, these two measurements are taken simultaneously using a single filtered spectrum. The high energy measurement corresponds to the following equation $$I_{M_H} = I_{M_H}^{(0)} e^{-(\mu_o d\alpha_o + \mu_w d\alpha_w + \mu_g d\alpha_g)}$$

where $I_{M_H}$ is the number at high energy counts detected by a measurement radiation detector, $I_{M_H}^{(0)}$ is the number of high energy counts when the radiation is passed through the empty sample cell, d is the diameter of the sample cell, $\alpha_o$ is the fluid phase fraction of oil, $\alpha_w$ is the fluid phase fraction of water, and $\alpha_o$ is the fluid phase fraction of gas. These fractions are unknown and are the subject of interest. The low energy measurement corresponds to the following equation $$I_{M_L} = I_{M_L}^{(0)} e^{-(\mu_o d\alpha_o + \mu_w d\alpha_w + \mu_g d\alpha_g)}$$

where $I_{M_L}$ is the number of low energy counts detected by a measurement radiation detector and $I_{M_L}^{(0)}$ is the number of low energy counts when the radiation is passed through the empty sample cell. Both of these equations can be solved to provide the following $$-\ln\left(\frac{I_{M_H}}{I_{M_H}^{(0)}}\right) = \mu_o d\alpha_o + \mu_w d\alpha_w + \mu_g d\alpha_g$$

for the high energy measurement and $$-\ln\left(\frac{I_{M_L}}{I_{M_L}^{(0)}}\right) = \mu_o d\alpha_o + \mu_w d\alpha_w + \mu_g d\alpha_g$$

for the low energy signal. Solving for both the high energy and low energy measurements, this provides two equations and three unknowns, so a further equation is needed to solve for the fluid fractions. The sample fluids comprise oil, water, and gas, so it is also known that $$\alpha_o + \alpha_w + \alpha_g = 1.$$

Using these three equations, the fluid fractions of oil, water, and gas can be determined based on the radiation passed through the sample.

Figure 3:
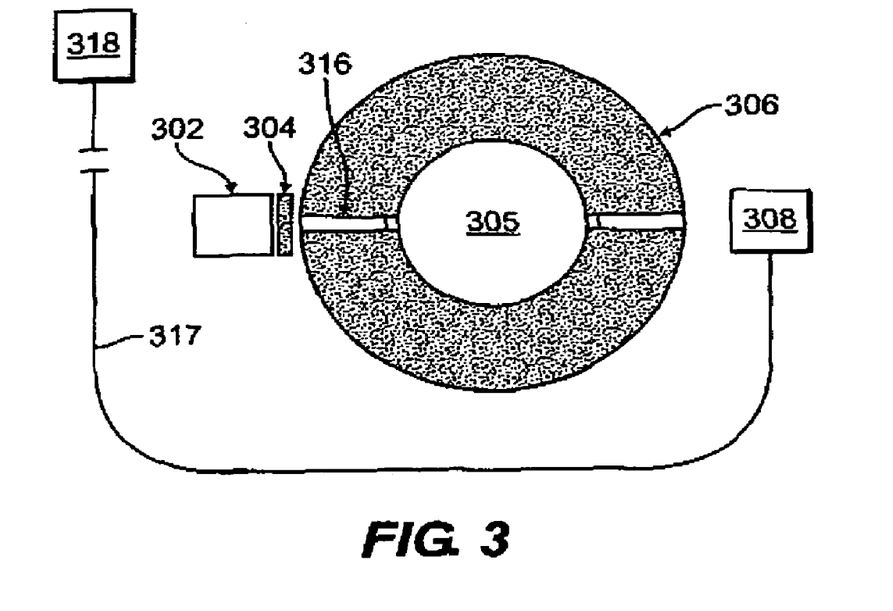
FIG. 3 is a schematic representation of one embodiment of the present invention.

One embodiment of the present invention is shown in FIG. 3. Sample fluid flows through channel 305 in a sample cell 306 which is, in this embodiment, a venturi chamber. In response to an input voltage, x-ray generator 302 creates radiation that is passed through filter 304. This filtered radiation then passes through path 316. Path 316 is a measurement path where radiation is passed through the sample cell 306 and sample fluid and on to measurement radiation detector 308. The output of measurement detector 308 is passed along line 317 to analysis unit 318. The tool may be used in a variety of different environments including laboratories, permanent monitoring at production sites, artificial lift optimization, receiving ports where it is desirable to determine a fluid fraction as fluid is delivered, etc.

Figure 4:
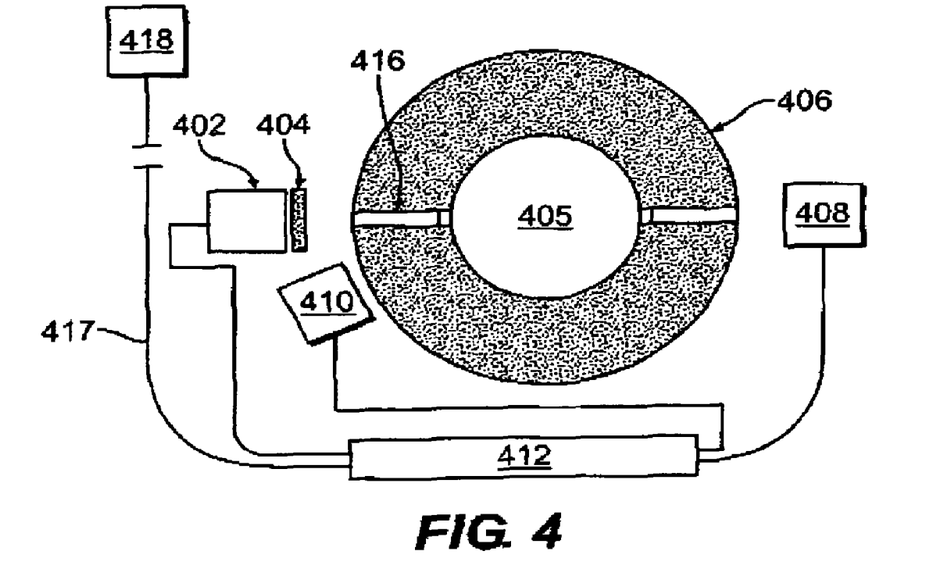
FIG. 4 is a schematic representation of another embodiment of the present invention comprising a reference detector.

Another embodiment of the invention is shown in FIG. 4. Sample fluid flows through channel 405 in a sample cell 406 which may be a venturi chamber. In response to an input voltage, x-ray generator creates radiation that is passed through filter 404. The filtered radiation then passes through measurement path 416, the sample cell 406 and sample fluid flowing through channel 405 and on to measurement radiation detector 408. Reference radiation detector 410 is positioned to detect the signal as it exits x-ray generator 402. In one embodiment, the outputs of the two radiation detectors are muted to a control and acquisition system 412. Information from this control system 412 is used in controlling the acceleration voltage of the x-ray generator 402 as well as the beam current of the x-ray generator. Some other functions of this control and acquisition system will be discussed below. Information from the detectors is forwarded along line 417 to an analysis unit 418.

Figure 5:
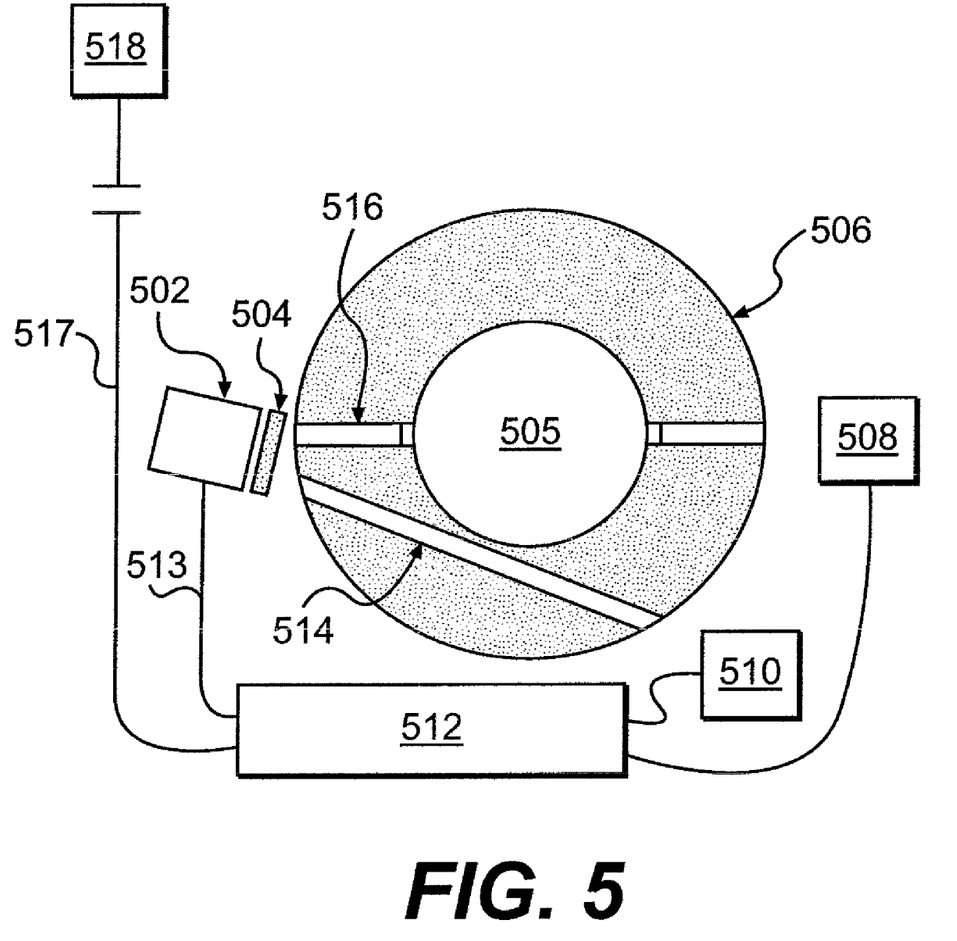
FIG. 5 is a schematic representation of another embodiment of the present invention comprising a reference detector and reference channel.

Another embodiment is shown in FIG. 5. Sample fluid flows through channel 505 in a sample cell 506 which is, in this embodiment, a venturi chamber. In response to this input voltage, x-ray generator 502 creates radiation that is passed through filter 504. This filtered radiation can then pass through two paths. Note that for optimal performance, x-ray generator 502 is positioned symmetrically with respect to the two paths to correct for any irregularities in the composition of filter 504. Path 516 is a measurement path where radiation is passed through the sample cell 506 and sample fluid flowing through channel 505 and on to measurement radiation detector 508. Path 514 is an optional reference path where radiation is passed directly from the x-ray generator 502 to a reference radiation detector 510. In one embodiment, the outputs of the two radiation detectors are routed to a control and acquisition system 512. Information from this control system 512 is routed via line 513 to the x-ray generator 502 to be used in controlling the acceleration voltage of the x-ray generator 502 as well as the beam current of the x-ray generator 502. Some other functions of this control and acquisition system will be discussed below. Information from the detectors is forwarded along wireline 517 to an analysis unit 518.

Figure 6:
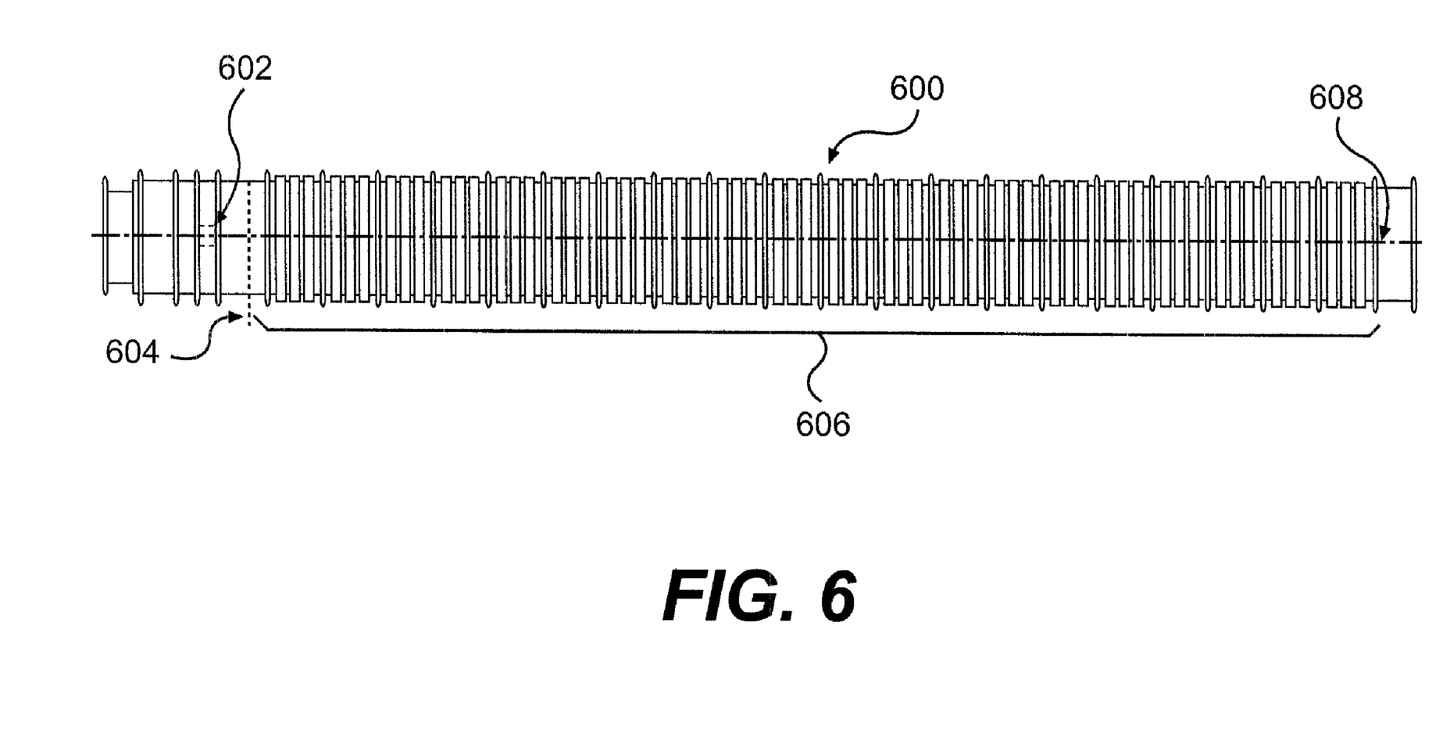
FIG. 6 is a schematic representation of one embodiment of an x-ray tube.

FIG. 6 shows an example of an x-ray tube 600 that may be used. Note that any x-ray tube may be used provided that the acceleration voltage and beam current can be controlled. This type of x-ray generator is referred to as a grounded target x-ray tube. Element 602 is a cathode that is operable to release electrons in response to exposure to heat. A high voltage generator applies a high voltage to cathode 602. The introduction of a small current heats the cathode 602 and causes it to release electrons. Grid 604 is operable to move electrons released from cathode 602 toward electron accelerating section 606. In one embodiment, this grid 604 is made of Nickel (Ni). Accelerating section 606 speeds electrons toward target 608. Upon collision with target 606, tube 600 generates x-rays suitable for use in the instant invention.

Figure 7:
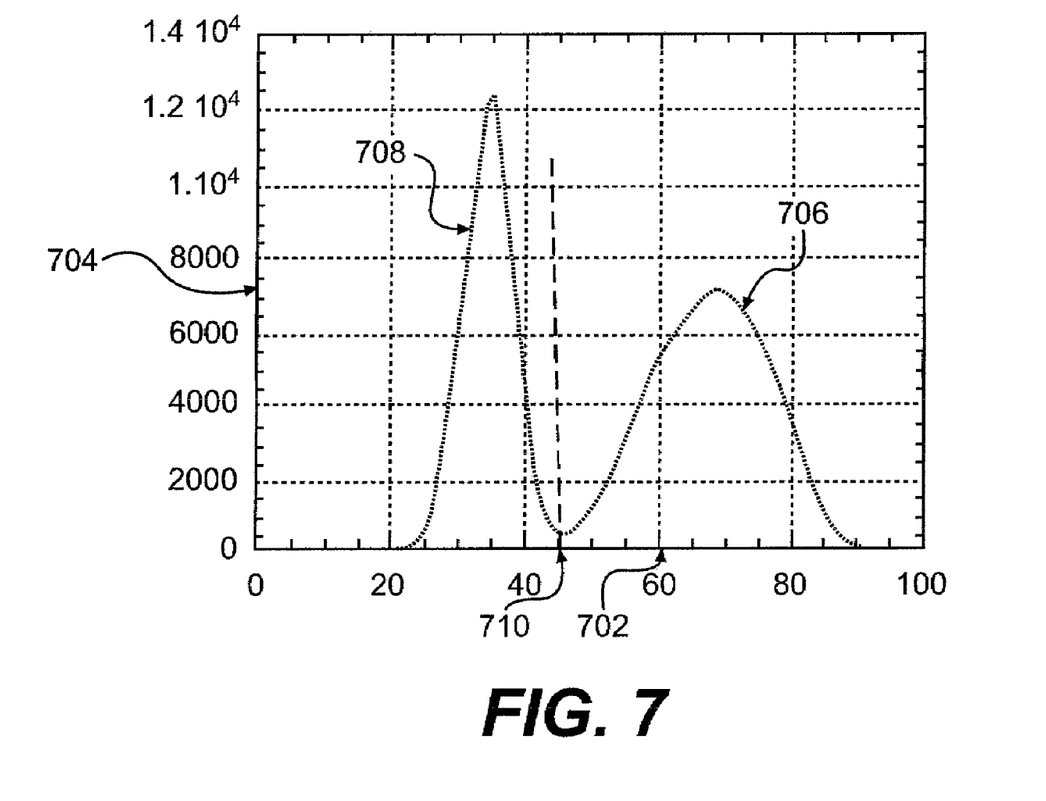
FIG. 7 is a graphic representation of a filtered radiation spectra used in determination of a fluid phase fraction.

As mentioned above, it is important to introduce a high energy signal and a low energy signal for proper determination of the fluid phase fraction. Filters 304, 404, and 504 allow this by filtering the radiation spectrum shown in FIG. 2. In one embodiment, the filter chosen is barium. However, any element can be used to filter the radiation as long as a high energy and low energy portion is provided. It is important to note, however, that depending on the desired voltage, certain elements may have too low or too high a K-edge to be effective in application. Assuming a barium filter is used, the resulting radiation spectrum is shown in FIG. 7. Axis 702 represents the energy in keV while axis 704 represents the number of counts per keV. The trace marked 708 shows the low energy portion of the signal. This can change depending on the element chosen for filter 304. Trace 706 represents the high energy portion of the signal.

Detectors 308, 408, 410, 508, and 510 all detect radiation and place all incident photons into either a high energy window or a low energy window. In one embodiment, the high energy window would be any energy above line 710 and the low energy window would be any energy below line 710.

As mentioned above, the invention can operate either as shown in FIG. 3, with no reference detector, or as in FIGS. 4 and 5, with a reference detector. In the embodiment of FIG. 3, the counts detected by the measurement radiation detector are used directly in the equations described above in determining the phase fractions of oil, water and gas. In the embodiment of FIGS. 4 and 5, the counts measured by reference detector 410 or 510 are used in normalizing the calculation. Specifically, the low energy and high energy measurement counts are divided by a low energy reference count, $I_{R_L}$, and a high energy reference count, $I_{R_H}$, respectively. Additionally, the counts measured through air are normalized in the same manner. This provides a more stable measurement because changes in the base output of the x-ray generator will be measured by the reference detector and used in normalizing the result.

The output of the reference detector is also used advantageously to control the acceleration voltage and beam current of x-ray generator 402. Please note that all functions of the reference detector are the same in the embodiments of FIGS. 4 and 5. The $I_{R_H}$ and $I_{R_L}$ are both proportional to the number of electrons hitting the target at any given time. Additionally, the ratio of $$\frac{I_{R_H}}{I_{R_L}}$$

is proportional to the acceleration voltage of the x-ray generator $V_{x\text{-}ray}$. Looking at FIG. 7, if the voltage of the x-ray generator decreased over time, the spectrum would shift somewhat to the left. This would cause less electrons to be placed in the high energy window and thus the ratio $$\frac{I_{R_H}}{I_{R_L}}$$

would decrease. This embodiment avoids this problem by monitoring this ratio, possibly in unit 412, and altering the acceleration voltage of the x-ray generator 402 to maintain a consistent spectrum.

In addition, it is important to carefully control the beam current output by the x-ray generator. This can also be controlled using the reference detector. The reference detector counts the number of incident photons in the high energy region and low energy region. The output of the reference detector can be used by either monitoring one of these counts or the sum of the two counts. The output of the reference detector is used to control the x-ray generator and ensure a constant beam current.

Radiation detectors 308, 408, 410, 508, and 510 can be any type of radiation detector capable of monitoring radiation and producing an output including grouping the electrons into a high and low energy window. In one embodiment, the radiation detector used is one of the type described in U.S. patent application Ser. No. 09/753,859 assigned to Schlumberger Technology Corporation. This disclosure is hereby incorporated by reference. This type of detector is advantageous for use downhole because it corrects its function with changing temperatures and conditions. This ensures that a constant reading can be obtained in any working environment.

Figure 8:
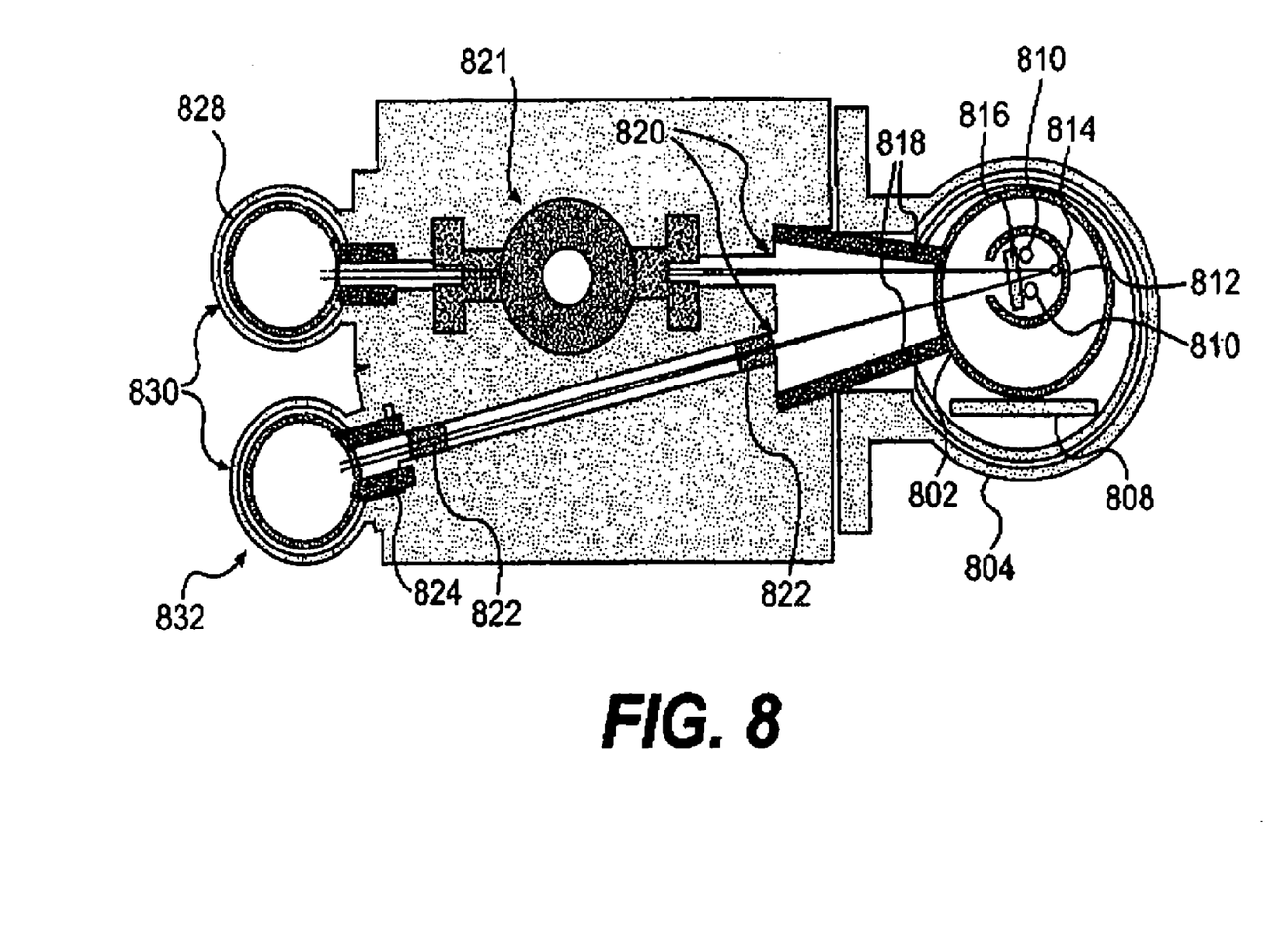
FIG. 8 is a detailed schematic representation of the structure of one embodiment of the invention.

As described, this invention is useful in a variety of locations. FIG. 8 shows one possible configuration. X-ray generator section 802 houses the x-ray tube that produces x-ray spot 814. Typically, 99% of the emission of the x-ray generator will be focused into this less than 2 mm diameter spot. Tungsten shield 812 and explosive proof housing 804 protect the outside environment from contamination by the radiation. It is important to ensure that the spot 814 remains stable and in a constant position. X-ray spot detectors 810 will recognize any stray radiation and alert of a possible problem with spot placement. Circuit board 808 is used in controlling the x-ray generator.

The radiation produced is passed through a filter 816 to provide a spectrum like the one shown in FIG. 7. Another safety feature is the alignment bars 818. These bars ensure that if the x-ray generator is removed from the device, it will stop producing radiation. The radiation passes through one of the channels 820. One radiation signal passes through sample cell 821 and on to measurement detector 828. The other signal passes directly to reference detector 832. Low density plugs 822 are used to ensure that the attenuation through the measurement and reference channel are identical when nothing is housed in sample cell 821. Another set of alignment bars 824 ensure that the radiation detectors cannot be removed while radiation is being produced. Finally, another explosion proof housing 830 surrounds the radiation detectors to increase operational safety.

The preceding description has been presented only to illustrate and describe the invention and some examples of its implementation. It is not intended to be exhaustive or to limit the invention to any precise form disclosed. Many modifications and variations are possible and would be envisioned by one of ordinary skill in the art in light of the above description and drawings.

The various aspects were chosen and described in order to best explain principles of the invention and its practical applications. The preceding description is intended to enable others skilled in the art to best utilize the invention in various embodiments and aspects and with various modifications as are suited to the particular use contemplated. It is intended that the scope of the invention be defined by the following claims; however, it is not intended that any order be presumed by the sequence of steps recited in the method claims unless a specific order is directly recited.

What is claimed is:

1. A tool for fluid fraction determination of multiphase fluid comprising:

an x-ray generator operable for producing a dual peak radiation spectrum having a low energy region and a high energy region;

a sample cell operably connected to said x-ray generator for receiving said dual peak radiation spectrum and serving to pass said dual peak radiation spectrum through a sample of said multiphase fluid inside said sample cell;

a measurement radiation detector operably connected to an output of said sample cell and being operable for measuring radiation transmitted through said sample cell and said sample of said multiphase fluid;

a reference radiation detector operably connected to an output of said x-ray generator, said reference radiation detector being configured to detect incident photons of said dual peak radiation spectrum not passed through said sample of said multiphase fluid to provide a reference output;

an analysis unit operably connected to said reference radiation detector and being configured to receive said reference output in order to maintain a constant, non-shifting dual peak radiation spectrum during operation of the x-ray generator;

wherein said reference output comprises counts of incident photons grouped into a high energy window and a low energy window, wherein photons above a set energy level will be added to a high energy reference count and photons below said set energy level will be added to a low energy reference count; and wherein an acceleration voltage of said x-ray generator is controlled by a ratio of the high energy reference count to the low energy reference count, and wherein a beam current of said x-ray generator is controlled by one of the high energy reference count, the low energy reference count, and the sum of the high energy reference count and low energy reference count.

2. The tool for fluid fraction determination as defined in claim 1, further comprising a filter operably connected to said x-ray generator and wherein said x-ray generator emits a bremstrahlung radiation spectrum that is passed through said filter to produce said dual peak radiation spectrum.

3. The tool of claim 2, wherein said filter is barium.

4. The tool for fluid fraction determination as defined in claim 1, wherein: said sample cell is a venturi chamber.

5. The tool for fluid fraction determination as defined in claim 1, wherein: said measurement radiation detector is configured to detect incident photons and provide a measurement output.

6. The tool for fluid fraction determination as defined in claim 5,
wherein said measurement output comprises counts of incident photons grouped into at least one of a high energy window and a low energy window, and
wherein photons above a set energy level will be added to a high energy measurement count and photons below said set energy level will be added to a low energy measurement count.

7. The tool for fluid fraction determination as defined in claim 6, wherein:
said analysis unit is further configured to determine a mass fraction or a volume fraction of at least one of a plurality of materials using said high energy measurement count and said low energy measurement count.

8. The tool of claim 7, wherein said sample cell comprises a measurement path for passing said dual peak radiation spectrum through said sample cell and said sample of said multiphase fluid to the measurement radiation detector and reference path for passing said dual peak radiation spectrum directly to said reference radiation detector.

9. The tool of claim 8, wherein said x-ray generator is positioned symmetrically with respect to said measurement path and said reference path.

10. The tool for fluid fraction determination as defined in claim 9, wherein: a mass fraction or a volume fraction of at least one of a plurality of materials is determined using a ratio of said high energy measurement count to said high energy reference count and a ratio of said low energy measurement count to said low energy reference count.

11. The tool for fluid fraction determination as defined in claim 7, wherein: said plurality of materials comprises oil, water, and gas.

12. A method for fluid fraction determination of a multiphase fluid comprising the steps of:
generating an input dual peak radiation spectrum comprising a high energy portion and a low energy portion;
passing said dual peak radiation spectrum through a sample of said multiphase fluid to produce an output radiation spectrum;
detecting said output radiation spectrum and determining a high energy photon count and a low energy photon count;
detecting said dual peak radiation spectrum;
normalizing the high energy photon count and low energy photon count using a high energy input radiation count and a low energy input radiation count;
calculating a ratio of the high energy input radiation count to the low energy input radiation count;
controlling an acceleration voltage of an x-ray generator used in said generating step based on said ratio;
controlling a beam current of said x-ray generator used in said generating step based on one of said high energy input radiation count and said low energy input radiation count and the sum of the high energy reference count and low energy reference count, and
determining the fluid fraction of at least one material in said sample of said multiphase fluid utilizing said high energy photon count and said low energy photon count,
wherein said control of said acceleration voltage and beam current maintains a constant, non-shifting dual peak radiation spectrum during operation of the x-ray generator.

13. The method for fluid analysis as defined in claim 12 wherein: said multiphase fluid comprises an oil, a water and a gas phase and said step of determining comprises solving the following system of equations:

$$-\ln\left(\frac{I_{M_H}}{I_{M_H}^{(0)}}\right) = \mu_o d\alpha_o + \mu_w d\alpha_w + \mu_g d\alpha_g$$

$$-\ln\left(\frac{I_{M_L}}{I_{M_L}^{(0)}}\right) = \mu_o d\alpha_o + \mu_w d\alpha_w + \mu_g d\alpha_g$$

$$\alpha_o + \alpha_w + \alpha_g = 1.$$

* * * * *